United States Patent
Barnett (10) Patent No.: US 8,827,985 B1
(45) Date of Patent: Sep. 9, 2014

(54) NON-BLADDER INVASIVE URETHRAL CATHETER SYSTEM

(71) Applicant: Henry Allison Barnett, Pike Road, AL (US)

(72) Inventor: Henry Allison Barnett, Pike Road, AL (US)

( * ) Notice: Subject to any disclaimer, the term of this patent is extended or adjusted under 35 U.S.C. 154(b) by 0 days.

(21) Appl. No.: 13/926,040

(22) Filed: Jun. 25, 2013

Related U.S. Application Data (60) Provisional application No. 61/771,231, filed on Mar. 1, 2013.

(51) Int. Cl.
*A61M 27/00* (2006.01)
*A61M 25/00* (2006.01)
*A61M 1/00* (2006.01)

(52) U.S. Cl.
CPC ............ *A61M 25/0017* (2013.01); *A61M 27/00* (2013.01); *A61M 1/00* (2013.01); *A61M 25/00* (2013.01)
USPC .......................................... 604/544; 604/317

(58) Field of Classification Search
CPC ... A61M 27/00; A61M 1/00; A61M 25/0017; A61M 25/00
USPC .......................... 604/541, 544, 19, 317, 99.04
See application file for complete search history.

(56) References Cited

U.S. PATENT DOCUMENTS

| | | | | |
|---|---|---|---|---|
| 3,543,759 A | * | 12/1970 | McWhorter | 604/100.01 |
| 3,811,450 A | * | 5/1974 | Lord | 604/102.03 |
| 4,932,938 A | | 6/1990 | Goldberg et al. | |
| 6,119,697 A | | 9/2000 | Engel et al. | |
| 6,972,040 B2 | * | 12/2005 | Rioux et al. | 623/23.66 |
| 8,500,684 B2 | * | 8/2013 | Gardner et al. | 604/99.04 |
| 2005/0107771 A1 | | 5/2005 | Finkbeiner | |
| 2008/0051762 A1 | * | 2/2008 | Tsukada et al. | 604/544 |
| 2009/0315864 A1 | * | 12/2009 | Silverbrook et al. | 345/179 |

FOREIGN PATENT DOCUMENTS

GB    2235383    6/1991

* cited by examiner

*Primary Examiner* — Tatyana Zalukaeva
*Assistant Examiner* — Benedict L Hanrahan
(74) *Attorney, Agent, or Firm* — Gerald M. Walsh; The Leo Law Firm (57) ABSTRACT

A non-bladder invasive urethral catheter system is provided as a system of apparatuses that provide a means relieving a user's urinary incontinence issues while reducing localized compression to the walls of their urethra. The non-bladder invasive urethral catheter system provides a more convenient and less intrusive means of enabling individuals suffering from urinary incontinence to live an ordinary life. The non-bladder invasive urethral catheter system provides the user with comfort and increased mobility and permits the user to maintain the indwelling catheter during urination. The apparatus blocks urine flow and leakage while installed within a user. The non-bladder invasive urethral catheter system utilizes several urethral catheters that are differentiated by the positioning of a urethral balloon element on the elongated body of the urethral catheter. Through the substitution of the differentiated urethral catheters, the user is able to reduce the trauma to a particular area of their urethra.

2 Claims, 8 Drawing Sheets

NON-BLADDER INVASIVE URETHRAL CATHETER SYSTEM

The current application claims a priority to the U.S. Provisional Patent application Ser. No. 61/771,231 filed on Mar. 1, 2013.

FIELD OF THE INVENTION

The present invention relates generally to a system of catheters, more particularly to a system of non-bladder invasive catheters that are positioned within the user's urethra to help relieve urinary incontinence and stenosis issues while reducing localized irritation to the walls of the urethra.

BACKGROUND OF THE INVENTION

Urinary incontinence is the involuntary leakage of urine. This condition has a number causes, including urethral strictures, bladder spasms, damaged muscles or nerves, an overactive bladder, prostate surgery, birth defects, polyuria, an enlarged prostate, radiation or drug treatments to the prostate, multiple sclerosis, spinal bifida, Parkinson's disease, stroke, spinal cord injury, old age, and many other diseases and injuries. Millions of individuals must deal with this problem on a daily basis. Although, methods, devices, and systems are provided in various prior art, many of these existing solution are unable to address the condition of urinary incontinence in a manner that does not incur additional pain, discomfort, and inconvenience to the user.

It is therefore the object of the present invention to provide a system of non-bladder invasive urethral catheters that are positioned within the user's urethra to help relieve urinary incontinence issues while reducing localized irritation to the walls of the urethra. The non-bladder invasive urethral catheter system provides a more convenient and less intrusive means of enabling individuals suffering from urinary incontinence to live an ordinary lifestyle. The non-bladder invasive urethral catheter system provides the user with comfort and increased mobility by providing a system that is non-bladder invasive and can remain within the user's urethra during urination. The non-bladder invasive urethral catheter system blocks urine flow or leakage until the user is ready to urinate, which in turn eliminates the need for a user to wear a diaper or a similar means of absorbing leakage. The non-bladder invasive urethral catheter system utilizes several urethral catheters that are differentiated by the positioning of a urethral balloon element on the elongated body of the urethral catheter. Through the substitution of the differentiated urethral catheters the user is able to reduce the trauma to a particular area of their urethra.

DETAIL DESCRIPTIONS OF THE INVENTION

All illustrations of the drawings are for the purpose of describing selected versions of the present invention and are not intended to limit the scope of the present invention.

Figure 1:
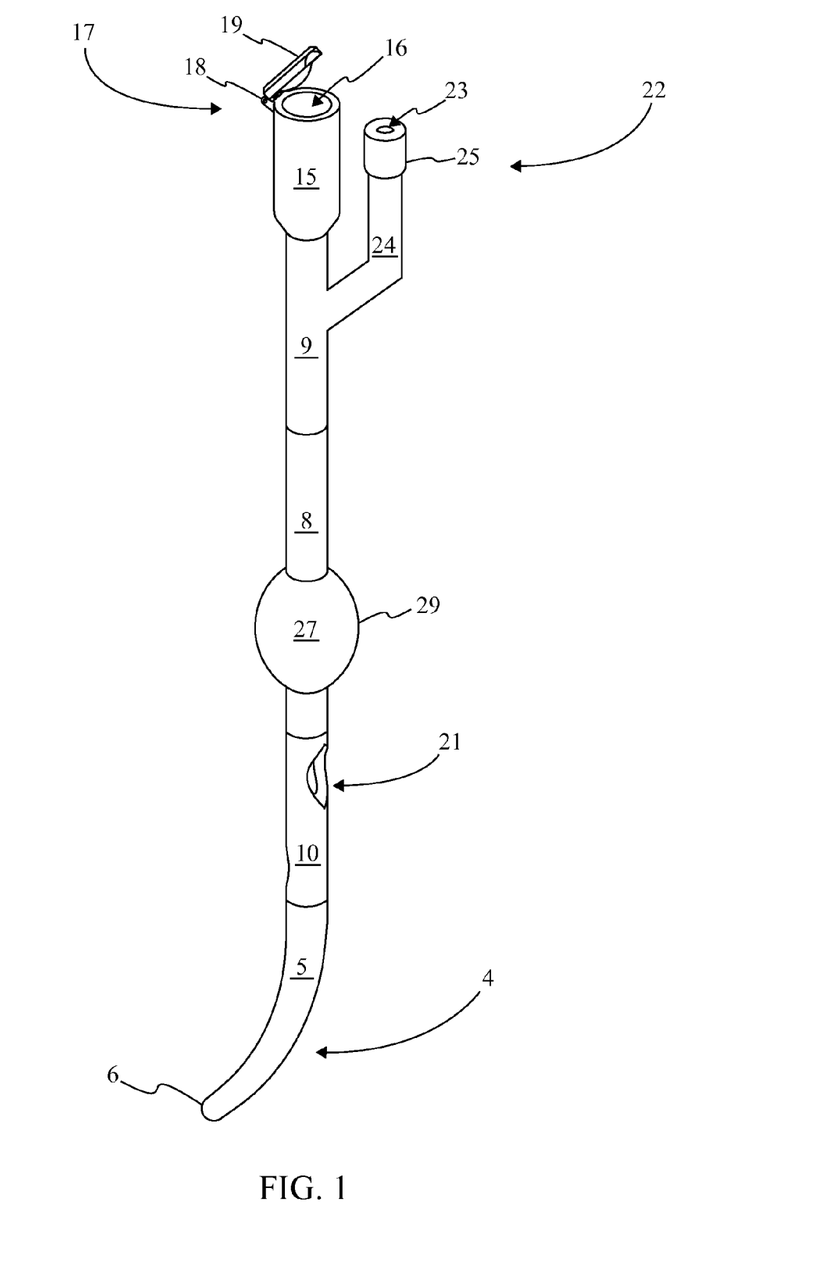
FIG. 1 is a front perspective view displaying the non-bladder invasive urethral catheter as per the current embodiment of the present invention.
Figure 2:
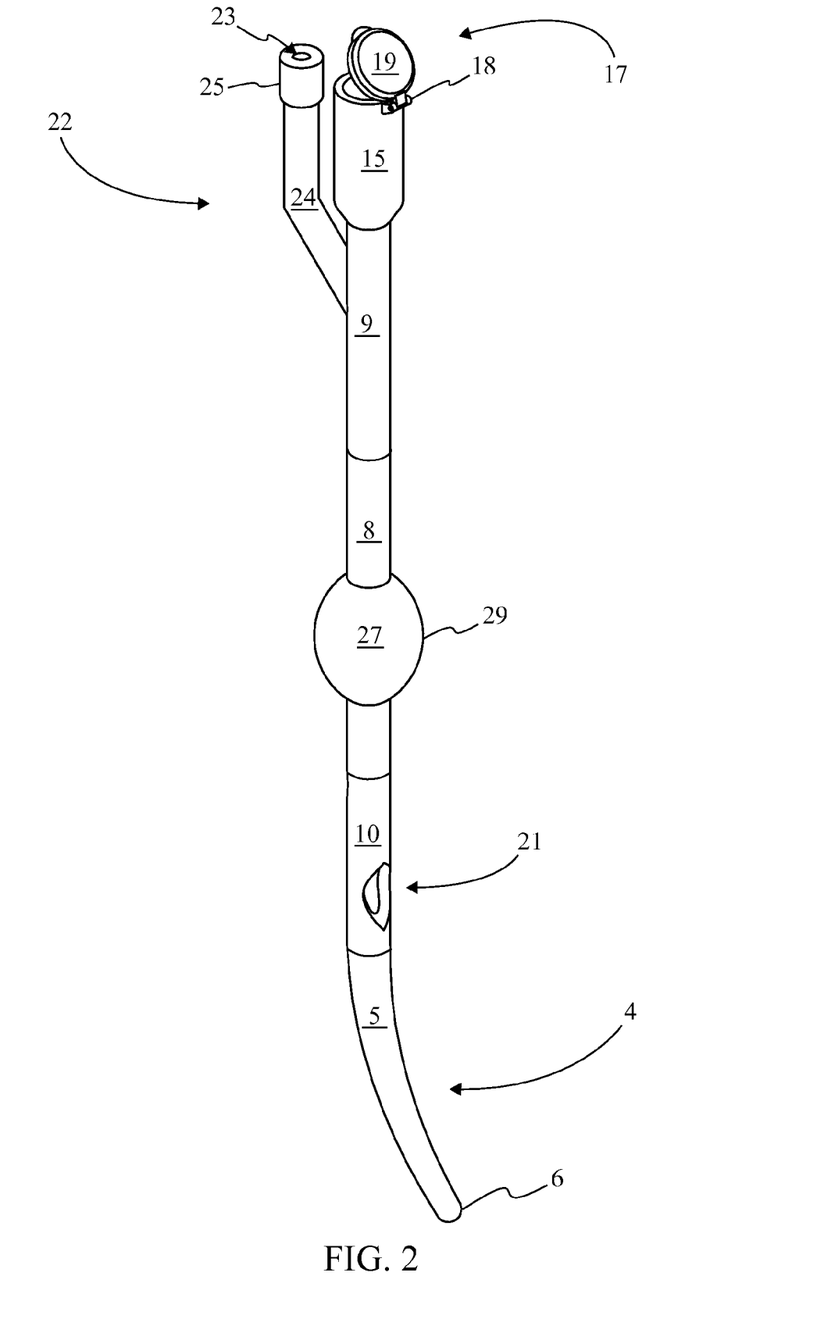
FIG. 2 is a rear perspective view displaying the non-bladder invasive urethral catheter as per the current embodiment of the present invention.
Figure 3:
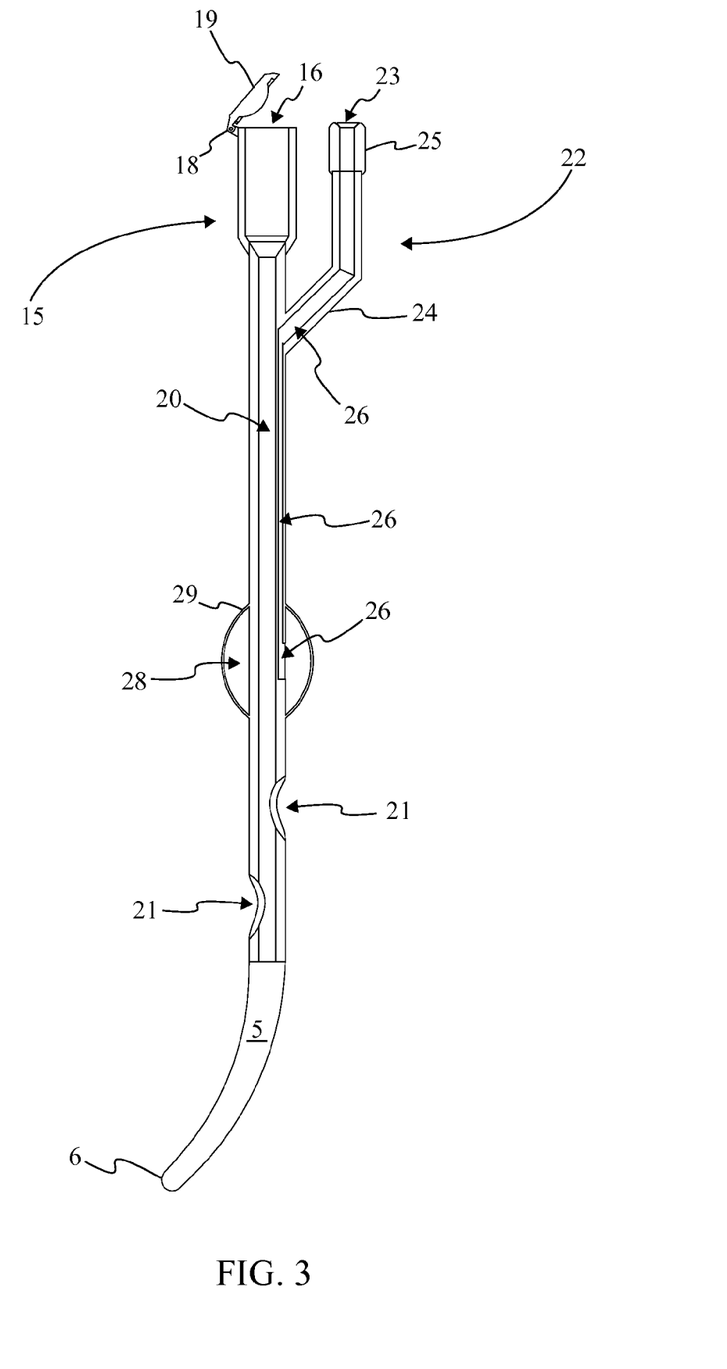
FIG. 3 is a cross sectional view displaying the non-bladder invasive urethral catheter as per the current embodiment of the present invention.

Referencing FIG. 1-FIG. 3, the present invention is a non-bladder invasive urethral catheter system that provides a user with a means of relieving urinary incontinence issues while reducing damage and injury caused to the urethra from localized pressure points associated with a urethral balloon element 27. In the current embodiment of the present invention, the non-bladder invasive urethral catheter system comprises a first urethral catheter 1, a second urethral catheter 2, and a third urethral catheter 3. the first urethral catheter 1, the second urethral catheter 2, and the third urethral catheter 3 each comprise an insertion tip 4, an elongated body 8, at least two urine inlets 21, a drainage lumen 20, a drainage assembly 15, an inflation assembly 22, an inflation lumen 26 and a urethral balloon element 27. The insertion tip 4 is a smooth rounded structure with a semi rigid construction that utilizes a particular curvature in order to guide the catheter through the urethra. The elongated body 8 is a cylindrical structure that is guided into the urethra by the insertion tip 4. The elongated body 8 is provided with a flexible construction and an appropriate diameter, relative to the user's urethra, in order to facilitate insertion and permit normal movement of the urethra with the indwelling catheter. The at least two urine inlets 21 are provided as fluid ducts that direct the user's urine into the catheter. The drainage lumen 20 is the provided as the fluid channel that transports the user's urine through the elongated body 8. The drainage assembly 15 is a terminal structure associated with the drainage lumen 20 that functions as the exhaust point for the user's urine. The inflation assembly 22 is a terminal structure associated with the inflation lumen 26 that permits fluid passage in order to inflate the urethral balloon element 27. The inflation lumen 26 is the fluid channel associated with fluid transport between the inflation assembly 22 and the urethral balloon element 27. The urethral balloon element 27 is the elastic structure that upon inflation permits the retention of the present invention within the user's urethra. The first urethral catheter 1, the second urethral catheter 2 and the third urethral catheter 3 contain similar component distribution but differ in the particular positioning of the urethral balloon element 27 relative to the elongated body 8. The shared component distribution allows the first urethral catheter 1, the second urethral catheter 2, and the third urethral catheter 3 to function as interchangeable components within the non-bladder invasive urethral catheter system.

Referencing FIG. 1-FIG. 3, the elongated body 8 is essential to the function of the present invention and is directly associated with the insertion tip 4, the at least two urine inlets 21, the drainage lumen 20, the drainage assembly 15, the inflation assembly 22, the inflation lumen 26, and the urethral balloon element 27. Both the drainage lumen 20 and the inflation lumen 26 are found positioned within the elongated body 8, wherein the elongated body 8 serves as the enclosure that houses both the drainage lumen 20 and the inflation lumen 26. The drainage lumen 20 traverses the length of the elongated body 8. The drainage lumen 20 is coincident with the drainage assembly 15 which is terminally positioned on the elongated body 8, opposite the at least two urine inlet. The at least two urine inlets 21 are also coincident with the drainage lumen 20 but are found peripherally positioned on the elongated body 8. The at least two urine inlets 21 are found positioned between the insertion tip 4 and the urethral balloon element 27. The at least two urine inlets 21 become coincident with the drainage lumen 20 by traversing the exterior portion of the elongated body 8. The coincident relation provided to the drainage assembly 15 and the at least two urine inlets 21 permit the drainage assembly 15 to be in fluid communication with the at least two urine inlets 21 by way of the drainage lumen 20. Additionally, the peripheral positioning of the at least two urine inlets 21 positions the at least two urine inlets 21 in a perpendicular arrangement to the drainage assembly 15, relative to the elongated body 8. The inflation assembly 22 is found positioned adjacent to the drainage assembly 15 but engaged peripherally to the elongated body 8. The inflation assembly 22 extends away from the exterior portion of the elongated body 8 forming an angled member. The inflation lumen 26 is positioned peripherally to the drainage lumen 20 within the elongated body 8. The inflation lumen 26 runs parallel to the drainage lumen 20 within the elongated body 8. The inflation lumen 26 is positioned between the inflation assembly 22 and the urethral balloon element 27. The urethral balloon element 27 is circumferentially positioned on the elongated body 8. The urethral balloon element 27 is positioned on the elongated body 8 between the at least two urine inlets 21 and the inflation assembly 22. The urethral balloon element 27 is coincident with inflation lumen 26. The coincident relation provided to the inflation assembly 22 and the urethral balloon element 27 permits the inflation assembly 22 to be in fluid communication with the urethral balloon element 27 by way of the inflation lumen 26.

Referencing FIG. 1 and FIG. 2, the elongated body 8 is a cylindrical structure that is provided with a flexible construction and an appropriate diameter, relative to the user's urethra, in order to facilitate insertion and permit normal movement of the urethra with the indwelling catheter. In the current embodiment of the present invention, the elongated body 8 comprises a distal end 9, a proximal end 10, and an inflation region 11. The distal end 9 represents the portion of the elongated body 8 that remains outside of the user's body while the proximal end 10 is the region that is found opposite but is positioned within the user's body. The distal end 9 is the region of the elongated body 8 that contains the drainage assembly 15 and the inflation assembly 22. The drainage assembly 15 is coupled to the terminal portion of the distal end 9 while the inflation assembly 22 is coupled to the peripheral portion of the distal end 9. The relation between the inflation assembly 22 and the distal end 9 provides the inflation assembly 22 as being extended away from the drainage assembly 15. The proximal end 10 serves as the attachment point for the at least two urine inlets 21 and the insertion tip 4. The insertion tip 4 is coupled to the terminal portion of the proximal end 10, wherein the engagement between the proximal end 10 and the insertion tip 4 seals the drainage lumen 20 allowing the at least two urine inlets 21 to function as the only means of fluid conveyance through the elongated body 8. Each of the at least two urine inlets 21 are peripherally positioned on the proximal end 10. The at least two urine inlets 21 are distributed equidistantly from each other on the proximal end 10. The at least two urine inlets 21 are found evenly spaced about the circumference of the proximal end 10, wherein the radian measurement between each of the at least two urine inlets 21 is congruent. The inflation region 11 is positioned between the proximal end 10 and the distal end 9. The inflation region 11 functions as the mounting point for the urethral balloon element 27. The inflation region 11 represents the region of the elongated body 8 where the positioning of the urethral balloon element 27 coincides with the user's urethra. The inflation region 11 provides a coincident relationship between the urethral balloon element 27 and the inflation lumen 26.

Referencing FIG. 1 and FIG. 2, the insertion tip 4, in the current embodiment of the present invention is provided as a semi rigid structure that guides the elongated body 8 into the user's urethra. The insertion tip 4 is found terminally positioned on the elongated body 8 opposite the positioning of the drainage assembly 15 and the inflation assembly 22. The insertion tip 4 is positioned adjacent to the at least two urine inlets 21 opposite the urethral balloon element 27. The insertion tip 4 is coupled to the terminal portion of the proximal end 10. In the current embodiment of the present invention, the insertion tip 4 comprises a curved tapered body 5 and a rounded end 6. The curved tapered body 5 provides facilitated insertion and catheterization of the present invention by reducing resistance during the insertion process. The curvature of the curved tapered body 5 coincides with the curvatures of the user's urethra, reducing discomfort felt by the user. The rounded end 6 functions as the blunt end of the curved tapered body 5 that evenly distributes pressure to the urethra around the curved tapered body 5 during insertion. The rounded end 6 is found terminally positioned on the curved tapered body 5 opposite the opposite the proximal end 10.

Figure 8:
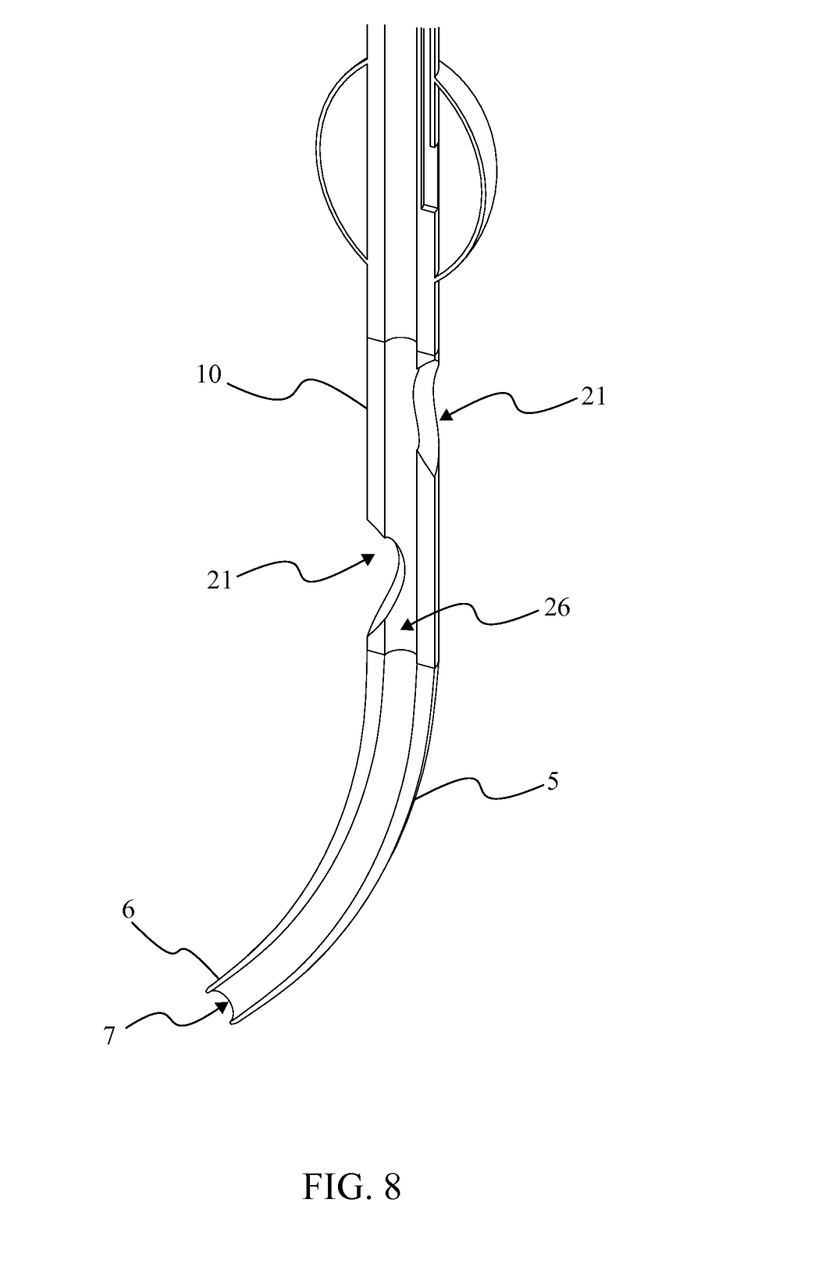
FIG. 8 is an enhanced cross sectional view displaying the insertion tip, the proximal end, and the inflation region as per the additional embodiment of the present invention.

Referencing FIG. 8, in an additional embodiment of the present invention, the insertion tip comprises an end channel 7. The end channel 7 functions as an extension of the drainage lumen 20 that allows a more direct avenue of fluid movement through the present invention. The end channel 7 is found positioned within the insertion tip 4 and traverses through the rounded end 6 and the curved tapered body 5. The end channel 7 is coincident with the drainage lumen 20 forming a conduit that spans the length of the present invention and terminates at the drainage assembly 15. It should be noted that the end channel 7 can be used in conjunction with the at least two urine inlets 21 as a means of improving fluid conveyance through the drainage lumen 20.

Figure 4:
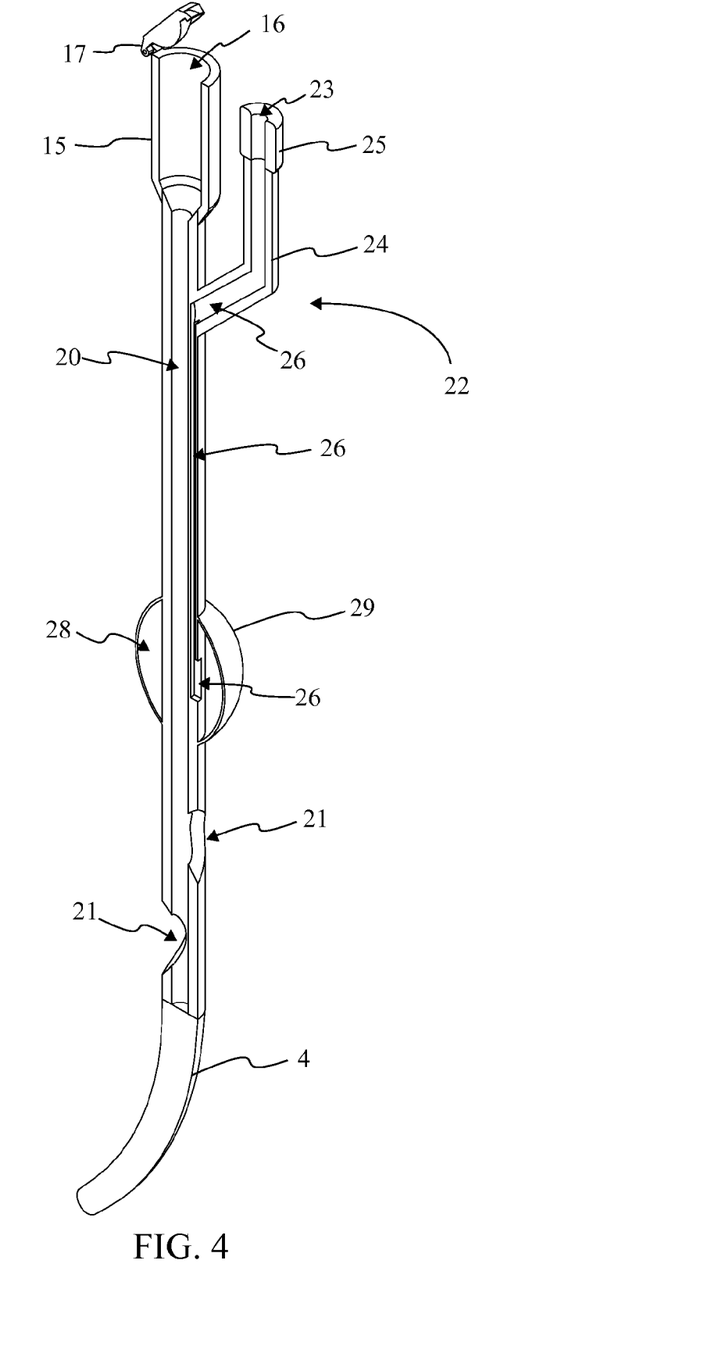
FIG. 4 is a cross sectional perspective view displaying the non-bladder invasive urethral catheter as per the current embodiment of the present invention.

Referencing FIG. 3 and FIG. 4, the at least two urine inlets 21 are provided as the apertures that permit fluid conveyance through the drainage lumen 20. Each of the at least two urine inlets 21 are peripherally positioned on the proximal end 10. The at least two urine inlets 21 are distributed equidistantly from each other on the proximal end 10 The at least two urine inlets 21 are found evenly spaced about the circumference of the proximal end 10, wherein the radian distance between each of the at least two urine inlets 21 neighboring each other is equal. It should be noted that while the current embodiment of the present invention is described as utilizing at least two urine inlets 21 that additional embodiments of the present invention may be configured to incorporate a singular urine inlet as well as accommodate as many urine inlets as needed. the drainage lumen 20 is provided as the fluid channel that transports the user's urine through the elongated body 8. The drainage lumen 20 is positioned within the elongated body 8 and extends from the proximal end 10 to the distal end 9. The drainage lumen 20 is positioned between the drainage assembly 15 and the at least two urine inlets 21. The drainage lumen 20 allows the at least two urine inlets 21 to be in fluid communication with the drainage assembly 15.

Referencing FIG. 1 and FIG. 3, the drainage assembly 15 is the terminal structure associated with the drainage lumen 20 that functions as the exhaust point for the user's urine. The drainage assembly 15 is in fluid communication with the at least two urine inlets 21 by way of the drainage lumen 20. The drainage assembly 15 is terminally positioned on distal end 9 of the elongated body 8. In the current embodiment of the present invention, the drainage assembly 15 comprises a drainage port 16 and a fluid impedance assembly 17. The drainage port 16 is the portion of the drainage assembly 15 that is coincident with the drainage lumen 20. The drainage port 16 allows the user's urine exit the present invention. The fluid impedance assembly 17 is the component structure that aligns with the drainage port 16 preventing the release of the users urine from the within the device. The fluid impedance assembly 17 is an essential component to the function of the present invention. The drainage assembly 15 can be provided in two embodiments that that are differentiated by the engagement means of the fluid impedance assembly 17 to the drainage port 16. The first embodiment provides the fluid impedance assembly 17 as an integrated component with the drainage port 16 while the second embodiment provides the fluid impedance assembly 17 as a detachable element to the drainage port 16. The first embodiment of the drainage assembly 15 allows fluid impedance assembly 17 to function as an integrated valve that restricts flow through the drainage port 16. The second embodiment of the drainage assembly 15 allows the fluid impedance assembly 17 to function as any means of restricting or preventing fluid flow through the drainage port 16 that can be detached from the drainage port 16 if desired. In the preferred embodiment of the present invention, the fluid impedance assembly 17 comprises a hinge 18 and a stopper cap 19. The hinge 18 is peripherally positioned on the drainage port 16. The hinge 18 is providing with an engagement to the stopper cap 19 and the peripheral edge of the drainage port 16. The hinge 18 enables the stopper cap 19 to be pivotally coupled to the drainage port 16 allowing the stopper cap 19 to form and impermeable seal with the drainage port 16 when engaged.

Referencing FIG. 1 and FIG. 3, the inflation assembly 22 is a terminal structure associated with the inflation lumen 26 that permits fluid passage in order to inflate the urethral balloon element 27. The inflation assembly 22 is peripherally positioned to the drainage assembly 15. The inflation assembly 22 is in fluid communication with the urethral balloon element 27 by way to the inflation lumen 26. The inflation assembly 22 is found positioned adjacent to the drainage assembly 15 but engaged peripherally to the distal end 9 of the elongated body 8. The inflation assembly 22 extends away from the exterior portion of distal end 9 forming an angled member. In the current embodiment of the present invention, the inflation assembly 22 comprises an elongated base 24, and inflation valve 25, and an inflation port 23. The elongated base 24 allows the inflation assembly 22 to be extended away from the drainage assembly 15. The elongated base 24 is peripherally positioned to the distal end 9. The inflation lumen 26 traverse through the elongated base 24 in order to become coincident with the inflation valve 25. The inflation valve 25 is the fluid restricting element that prevents air/fluid from escaping the urethral balloon element 27 through the inflation lumen 26. The inflation valve 25 is positioned between the elongated base 24 and the inflation port 23. The inflation valve 25 is coincident with the inflation lumen 26 and provides the inflation port 23 with a means of fluid communication with the inflation lumen 26.

Referencing FIG. 3 and FIG. 4, the inflation lumen 26 is the fluid channel associated with fluid transport between the inflation assembly 22 and the urethral balloon element 27. The inflation lumen 26 is positioned between the urethral balloon element 27 and the inflation assembly 22. The inflation lumen 26 provides the inflation assembly 22 with a means of fluid communication with the urethral balloon element 27. The inflation lumen 26 is found positioned within the elongated body 8 but positioned peripherally to the drainage lumen 20. The inflation lumen 26 traverses the elongated body 8 from the inflation region 11 to the distal end 9. The inflation lumen 26 runs parallel to the drainage lumen 20 but diverts into the elongated base 24 of the inflation assembly 22 and ends coincident with the inflation region 11 of the elongated body 8.

Referencing FIG. 3 and FIG. 4, the urethral balloon element 27 is the elastic structure that upon inflation permits the retention of the present invention within the user's urethra. The urethral balloon element 27 is a bulb shaped fluid filled bladder. The urethral balloon element 27 is in fluid communication with the inflation assembly 22 by way of the inflation lumen 26. The urethral balloon element 27 is circumferentially positioned on the inflation region 11 of the elongated body 8, wherein the urethral balloon element 27 is concentric with the inflation region 11 of the elongated body 8. In the current embodiment of the present invention, the urethral balloon element 27 comprises an elastic exterior 29 and a fluid filled chamber. The elastic exterior 29 is the outer portion of the urethral balloon element 27 that becomes coincident with the user's urethra when inflated. The elastic exterior 29 hermetically encloses the fluid chamber 28 against the inflation region 11 of the elongated body 8. The fluid chamber 28 is in fluid communication with the inflation lumen 26.

Figure 5:
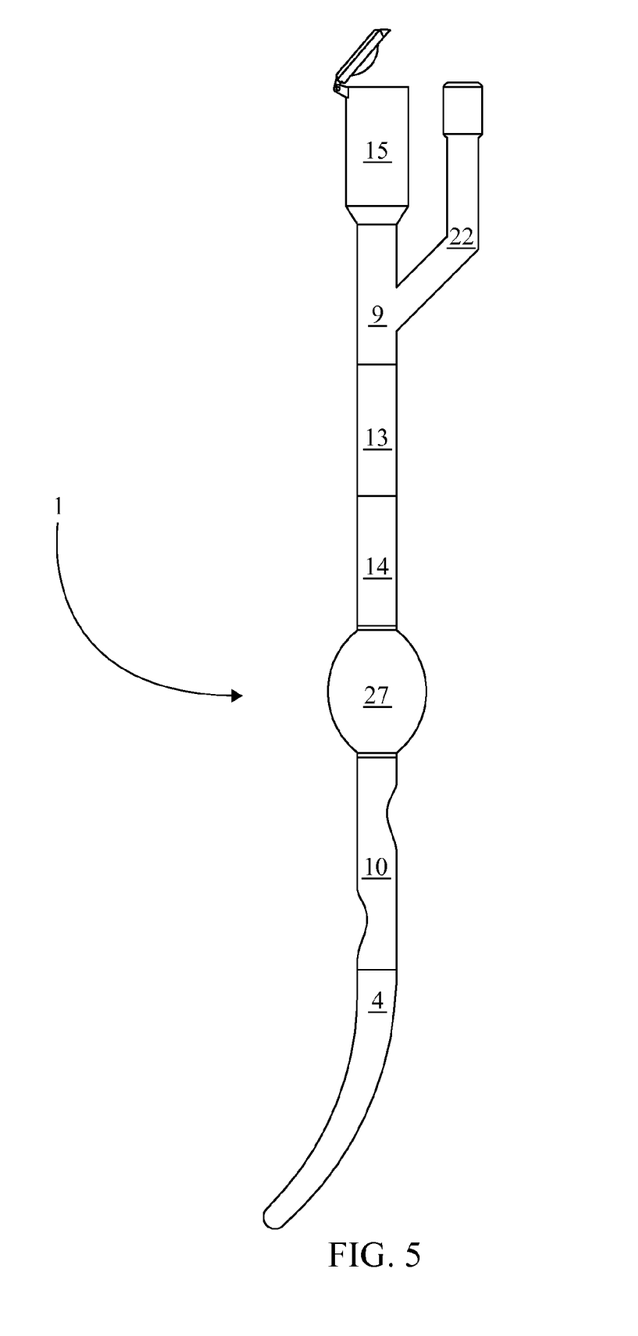
FIG. 5 is a front elevational view displaying the first urethral catheter configured as per the preferred embodiment of the present invention.
Figure 6:
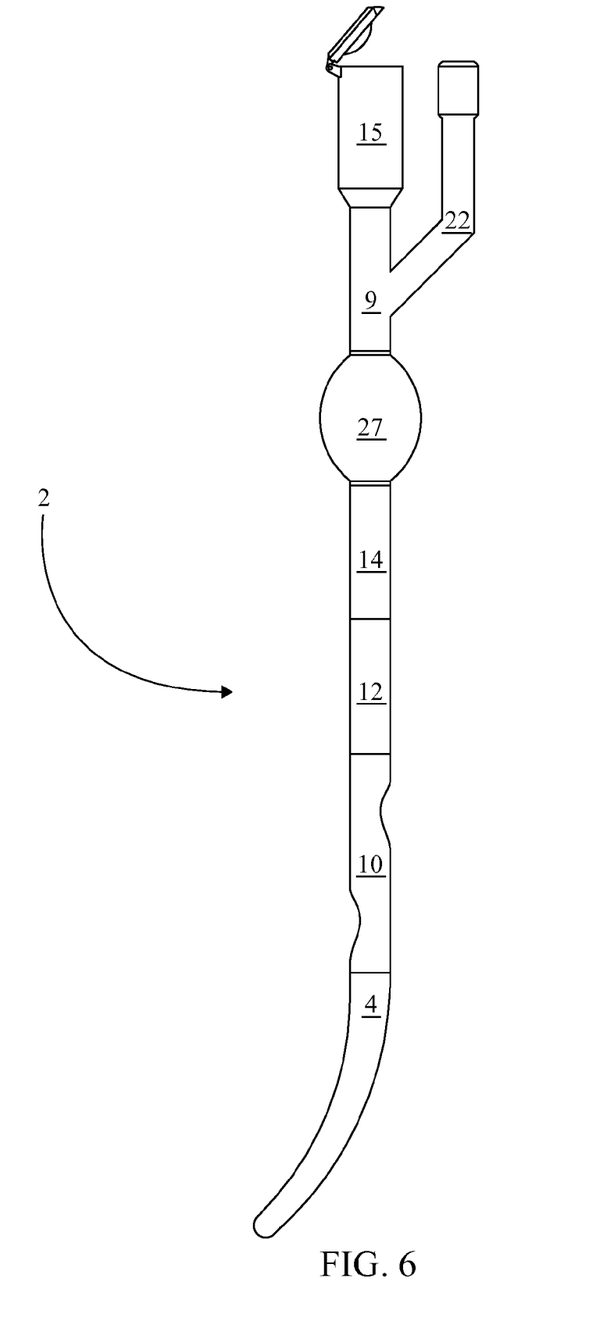
FIG. 6 is a front elevational view displaying the second urethral catheter configured as per the preferred embodiment of the present invention.
Figure 7:
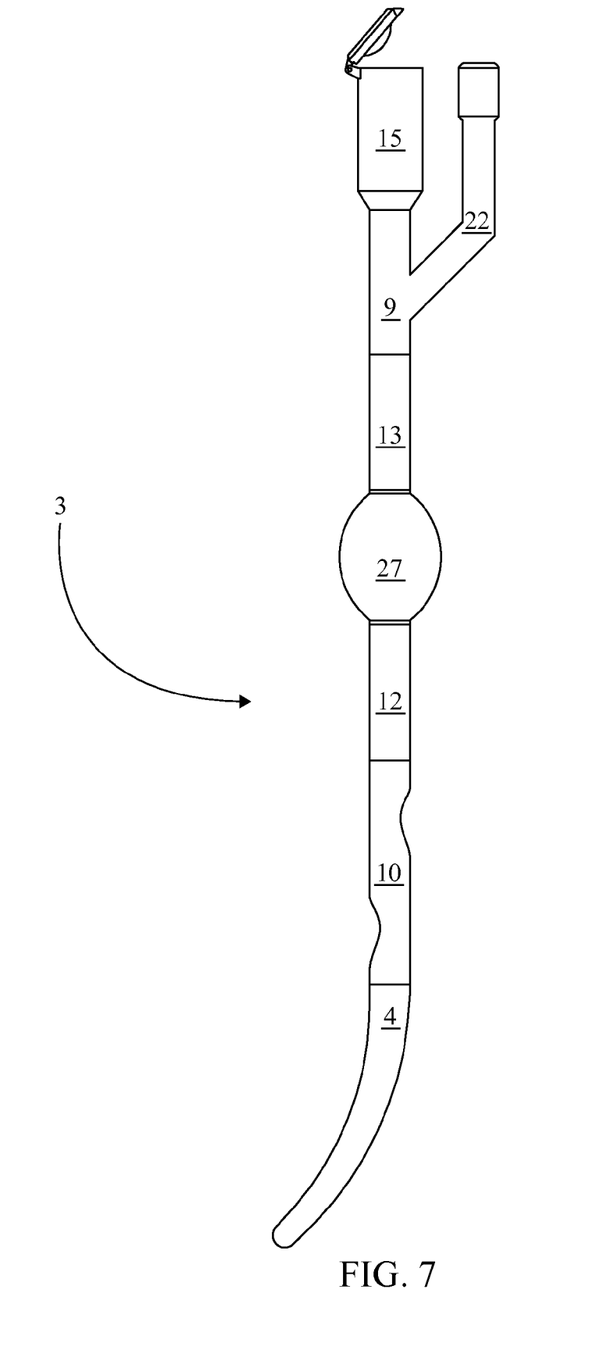
FIG. 7 is a front elevational view displaying the third urethral catheter configured as per the preferred embodiment of the present invention.

Referencing FIG. 5-FIG. 7, the inflation region 11 is the area of the elongated body 8 that contains the urethral balloon element 27. In the current embodiment of the present invention, the inflation region 11 comprises a first section 12, a second section 13, and a third section 14. The first section 12, the second section 13, and the third section 14, correspond to distinct areas of the inflation region 11 where the urethral balloon element 27 is mounted. The positioning of the urethral balloon element 27 on either the first section 12, the second section 13, or the third section 14, differentiates the urethral catheter as being the first urethral catheter 1, the second urethral catheter 2 and the third urethral catheter 3. The first urethral catheter 1 contains the urethral balloon element 27 positioned coincident with the first section 12 of the inflation region 11. The second urethral catheter 2 contains the urethral balloon element 27 positioned coincident with the second section 13 of the inflation region 11. The third urethral catheter 3 contains the urethral balloon element 27 positioned coincident with the third section 14 of the inflation region 11. the distinction of between the first urethral catheter 1, the second urethral catheter 2 and the third urethral catheter 3 provides the system with a means of reducing the localized pressure to the urethra as a result of the positioning of the urethral balloon element 27.

Referencing FIG. 5-FIG. 7, in the preferred embodiment of the present invention, the non-bladder invasive urethral catheter system provides the present invention with a means of reducing localized pressure points within the user's urethra as a result of the urethral balloon element 27 positioning. The present invention accomplishes this through the interchangeable use of the first urethral catheter 1, the second urethral catheter 2 and the third urethral catheter 3. The user would utilize each of the non-bladder invasive catheters in similar manner. The user would stop using a particular catheter after a predetermined amount of time and then substitute it for another catheter. Due to the specific positioning of the urethral balloon element 27 on the inflation region 11, each catheter in the non-bladder invasive urethral catheter system would be coincident with a different section of the user's urethra. By alternating the use of each of the urethral catheters, the non-bladder invasive urethral catheter system would reduce localized compression associated with use of a urethral balloon catheter.

The current embodiment of the present invention has several advantages over incontinence devices disclosed in prior art. The present invention blocks urine flow or leakage until the user is ready to urinate, which in turn eliminates the need for a user to wear a diaper or a similar means of absorbing leakage. the present invention permits a user to urinate without having to remove the and reinsert the indwelling catheter, which in turn eliminates or significantly reduces irritation, pain, discomfort, and infections, caused by frequent re-catheterization. This benefit also enables a user to travel without having to carry a large supply of catheters. A user may also participate in a large range of activities with the indwelling catheter such as swimming, and can additionally be removed as needed to allow for other activities such as sexual intercourse.

In the current embodiment of the present invention, the non-bladder invasive urethral catheter system is specifically designed to address male urinary incontinence and stenosis issues. The combination of the elongated body 8 and the insertion tip 4 are particularly sized in order to be inserted through the penile portion of a male user's urethra. In the current embodiment of the present invention the insertion tip 4 is specifically designed to traverse through the male user's urethra but is provided in a manner that prevents the insertion tip 4 from traversing into the bladder. The flexible nature of the elongated body 8 reduces irritation to the base of the user's urethra. During use, the inflated urethral balloon element 27 would form a seal within the user's urethra preventing urine from traversing around the elongated body 8. The user's urine would be directed into the drainage lumen 20 by the at least two urine inlets 21. Once in the drainage lumen 20 the urine would be prevented from being excruciated by the drainage assembly 15. The engagement of the fluid impedance assembly 17 to the drainage port 16 would prevent urine flow out of the present invention until the user was ready to urinate. Although the present invention is specifically designed for use in male users, it should be noted that the component distribution allows configuration for use in female users. In this additional embodiment, the curvature of the curved tapered body 5 would be reduced to accommodate the more linear path of the female urethra. Both the insertion tip 4 and the elongated body 8 would be shortened in order to more adequately conform to the length of a female user's urethra. Furthermore, additional components may be included in order to provide a more secure means of retaining the present invention within female users. These additional components may be associated utilizes the inflation assembly 22, the inflation lumen 26, and/or the urethral balloon element 27 in order to provide a gender specific means of resolving urinary incontinence issues.

In the current embodiment of the present invention, the fluid impedance assembly 17 is described as having two engagement configurations with the drainage port 16, wherein the fluid impedance assembly 17 can be provided with a detachably coupling to the drainage port 16 or as an integrated component built into the drainage port 16. while the preferred embodiment of the present invention describes a pivoting stopper cap 19 that is coupled to the peripheral portion of the drainage port 16, additional embodiments may incorporate a different component system that would either detachably couple to the drainage port 16 or be provided as an integrated component that cooperatively functions with the drainage port 16. In an additional embodiment of the present invention where the fluid impedance assembly 17 is provided as a integrated component, the fluid impedance assembly 17 could be provided as a valve system that can include but are not limited to compression valves and twist valves. In an additional embodiment of the present invention where the fluid impedance assembly 17 is provided with a detachable engagement to the drainage port 16, the fluid impedance assembly 17 can be provided as a stopper or a seal that can include but is not limited to a screw on cap or stopper plug.

In an additional embodiment of the present invention, the at least two urine inlets 21 comprise a narrow end and a wide end. the narrow end and the wide end provide each of the at least two urine inlets 21 with a particular tear drop shape that is able to more efficiently direct fluids into the drainage lumen 20. The tear drop shape provides the narrow end oriented towards the proximal end 10 and with the wide end oriented towards the distal end 9.

Although the invention has been explained in relation to its preferred embodiment, it is to be understood that many other possible modifications and variations can be made without departing from the spirit and scope of the invention as hereinafter claimed.

What is claimed is:

1. A non-bladder invasive urethral catheter system comprises comprising:
 a first urethral catheter;
 a second urethral catheter;
 a third urethral catheter;
 the first urethral catheter, the second urethral catheter, and the third urethral catheter each comprising an elongated body with a drainage lumen and an inflation lumen, wherein said drainage lumen has one or more urine inlets and a drainage assembly, wherein said inflation lumen has a urethral balloon element and a balloon inflation assembly, and wherein said elongated body has an insertion tip;
 said elongated body having a distal end, a proximal end, and a central portion therebetween, wherein said drainage assembly and said balloon inflation assembly are near said distal end, said insertion tip and said one or more urine inlets are near said proximal end, and said urethral balloon element is circumferentially positioned on said central portion between said one or more urine inlets and said drainage assembly;
 said elongated body being constructed so that said insertion tip is prevented from entering the bladder when said urethral catheter is positioned in a urethra of a user;
 said urethral balloon element being inflated and deflated by means of said balloon inflation assembly, wherein, when said urethral balloon element is positioned in said urethra and is inflated, said urethral balloon element is constructed to form a seal within the user's urethra preventing urine from traversing around said elongated body, to cause urine to flow through said one or more urine inlets, and to cause said urethral catheter to remain in said urethra;
 the drainage assembly comprises a drainage port and a fluid impedance assembly;
 the inflation assembly comprises an elongated base, an inflation valve, and an inflation port;
 the urethral balloon element comprises a fluid chamber and an elastic exterior;

both the drainage lumen and the inflation lumen being positioned within the elongated body;

the inflation lumen being peripherally positioned to the drainage lumen;

the drainage assembly being positioned adjacent to the inflation assembly;

the inflation assembly being peripherally positioned to the drainage assembly;

the drainage lumen being positioned between the drainage assembly and the one or more urine inlets;

the drainage assembly being in fluid communication with the one or more urine inlets by way of the drainage lumen;

the inflation lumen being positioned between the inflation assembly and the urethral balloon element;

the inflation assembly being in fluid communication with the urethral balloon element by way of the inflation lumen;

the one or more urine inlets being peripherally positioned on the elongated body;

the one or more urine inlets traverse traversing the elongated body into the drainage lumen;

the urethral balloon element being positioned between the one or more urine inlets and inflation assembly;

the one or more urine inlets being positioned between the insertion tip and the urethral balloon element; and the first urethral catheter, the second urethral catheter, and the third urethral catheter being different from each other in that the position of said urethral balloon element on said central portion is different among said first urethral catheter, said second urethral catheter, and said third urethral catheter so that each said first urethral catheter, said second urethral catheter, and said third urethral catheter has a urethral balloon element being coincident with a different section of said user's urethra compared to the others, wherein trauma to a particular area of said urethra, caused by said balloon element, is minimized by replacing said first urethral catheter, said second urethral catheter, and said third urethral catheter with each other.

2. The non-bladder invasive urethral catheter system as claimed in claim 1 further comprising said insertion tip being tapered.

* * * * *